(12) United States Patent
Prater et al.

(10) Patent No.: US 7,704,948 B2
(45) Date of Patent: Apr. 27, 2010

(54) PHARMACEUTICAL COMPOSITION

(75) Inventors: Derek Allan Prater, Cambridgeshire (GB); Hassan Mohammed, Cambridgeshire (GB); Malcolm Walden, Cambridgeshire (GB); Geoff Hayes, Essex (GB); Harjit Tamber, Hertfordshire (GB)

(73) Assignee: Euro-Celtique S.A., Luxembourg (LU)

( * ) Notice: Subject to any disclaimer, the term of this patent is extended or adjusted under 35 U.S.C. 154(b) by 1000 days.

(21) Appl. No.: 10/479,069

(22) PCT Filed: May 30, 2002

(86) PCT No.: PCT/GB02/02623

§ 371 (c)(1), (2), (4) Date: May 19, 2004

(87) PCT Pub. No.: WO02/096394

PCT Pub. Date: Dec. 5, 2002

(65) Prior Publication Data

US 2004/0197406 A1 Oct. 7, 2004

(30) Foreign Application Priority Data

May 30, 2001 (GB) ................................ 0113074.9
Dec. 24, 2001 (GB) ................................ 0130957.4
May 13, 2002 (GB) ................................ 0210905.6

(51) Int. Cl.
*A61K 31/13* (2006.01)
*A61K 31/132* (2006.01)
*A61K 31/436* (2006.01)
*C12Q 1/48* (2006.01)

(52) U.S. Cl. .................. 514/11; 514/291; 514/659; 435/15

(58) Field of Classification Search .................. None
See application file for complete search history.

(56) References Cited

U.S. PATENT DOCUMENTS

| 4,786,505 | A |   | 11/1988 | Lovgren et al. ............. 424/468 |
|---|---|---|---|---|
| 5,525,355 | A | * | 6/1996 | Brown et al. ............... 424/456 |
| 5,651,983 | A |   | 7/1997 | Kelm et al. |
| 5,656,290 | A | * | 8/1997 | Kelm et al. ................. 424/456 |
| 5,670,158 | A |   | 9/1997 | Davis et al. ................. 424/400 |
| 5,843,479 | A | * | 12/1998 | Kelm et al. ................. 424/479 |
| 6,136,347 | A | * | 10/2000 | Pollinger et al. ............ 424/495 |
| 7,314,640 | B2 | * | 1/2008 | Sriwongjanya et al. ..... 424/490 |
| 2007/0009582 | A1 | * | 1/2007 | Madsen et al. ............. 424/445 |

FOREIGN PATENT DOCUMENTS

| EP | 0682946 | 11/1995 |
|---|---|---|
| JP | 57099521 | 6/1982 |
| JP | 7165561 | 6/1995 |
| JP | 11506433 | 6/1999 |
| WO | WO 98/16229 | 4/1998 |
| WO | 0067747 | 11/2000 |
| WO | 0078284 | 12/2000 |

OTHER PUBLICATIONS

Seishichi Uemura, et al., "New Water dispersion type enteric film formulation, Eduragit L30D-55," Recent Formulations Technology and Application I, Sep. 1, 1983, pp. 129-131.

* cited by examiner

*Primary Examiner*—Brian-Yong S Kwon
(74) *Attorney, Agent, or Firm*—Davidson, Davidson & Kappel, LLC

(57) ABSTRACT

A stool softener and enteric coated bisacodyl form of a pharmaceutical composition.

14 Claims, 2 Drawing Sheets

PHARMACEUTICAL COMPOSITION

The present invention relates to a pharmaceutical composition. More particularly, this invention relates to a laxative composition, to processes for preparing laxative compositions, and to intermediate formulations for use in preparing finished pharmaceutical products.

BACKGROUND OF THE INVENTION

Combinations of stimulant laxatives and stool softeners are known on the market. For example, co-danthramer capsules and suspensions contain danthron and poloxamer (polyoxyethylene-polyoxypropylene block copolymers), and co-docusate capsules contain danthron and docusate sodium. These products have been effective in treating constipation, especially in the elderly and in patients suffering constipation resulting from administration of opioid analgesics. Such combination products have a reputation of being effective yet gentle. However the regulatory authorities have increasingly scrutinised the safety of stimulant laxatives and have restricted the indications of danthron-containing laxatives to cancer patients. Preparations containing phenolphthalein have been removed from many markets due to concern over potential carcinogenicity. Carcinogenicity testing has been conducted or is in progress with other stimulant laxatives and it is likely that other molecules will be subject to restriction of indications or removal from the market.

Bisacodyl is a diphenylmethane stimulant laxative used for the treatment of constipation and bowel evacuation. It acts mainly in the large intestine within 6-12 hours following oral administration. Bisacodyl was recently subjected to carcinogenicity testing and was shown to be free of carcinogenic/mutagenic potential and therefore, from a safety perspective, is the stimulant laxative of choice. However bisacodyl is directly irritant to the intestinal mucosa of the upper intestine and can cause griping and epigastric pain. To reduce the incidence of such effects bisacodyl is conventionally administered as enteric-coated tablets (e.g. Dulcolax, Boehringer), in doses of 5-15 mg daily. Due to the reported irritant nature of the active compound and the drug sensitivity to the low pH of the gastric environment, tablets have to be swallowed whole and not within one hour of milk or antacids. Bisacodyl is also available as suppositories, with onset of action within 20-60 minutes, but not as a commercially available oral liquid or sachet.

The enteric coated dosage forms do not lend themselves to combination products. A combination product of enteric coated bisacodyl with poloxamer is particularly difficult since the latter is a high dose, waxy, low melting point solid, which cannot be readily formulated into a solid dosage form of suitable size for acceptance by the patient.

A bisacodyl combination formulation can be made by the method of our EP-A 642,786, which involves melting a normally solid stool softener, such as a poloxamer, dispersing/dissolving the bisacodyl or other stimulant laxative in the melt, filling capsule shells, and allowing the capsules to cool. Such a product will have advantages with regard to dosage form and other properties. However, we have unexpectedly found that bisacodyl is unstable in poloxamer and also that the bisacodyl and poloxamer interact, with the degradation of the bisacodyl being accelerated in the presence of poloxamer. Preparation of capsules containing a hot melt of bisacodyl and poloxamer (as used for co-danthramer capsules), which are then enteric coated is therefore unlikely to produce a product that is chemically stable and has a satisfactory shelf life. Furthermore production scale enteric coating of capsules containing a low melting point, waxy, solid is very difficult due to melting and leakage or softening and deformation of the waxy, low melting point poloxamer.

SUMMARY OF THE INVENTION

The present invention provides pharmaceutical compositions which comprise stool softener and enteric coated bisacodyl. Typical compositions include enteric coated particles of bisacodyl or enteric coated tablets of bisacodyl. Enteric coated bisacodyl particles or tablets are part of this invention as intermediate formulations for use in the manufacture of finished pharmaceutical compositions further comprising a stool softener.

For preference, the bisacodyl is stabilised against degradation caused by the enteric coating. Thus, for enhanced stability, it may be appropriate to include a barrier coating between the bisacodyl cores and the enteric coating, and/or to include an overcoat on the enteric coated bisacodyl particles or enteric coated tablets of bisacodyl. Tablets made from the aforementioned enteric coated particles are also part of this invention, though currently we prefer enteric coated tablets made from bisacodyl cores.

The present invention can provide a safe and effective, yet gentle laxative, by utilising a lower dose of enteric coated bisacodyl combined with a stool softener. The finished formulation can take the form of a filled capsule. The fill can be stool softener and the enteric coated particles or enteric coated tablets.

The invention further provides methods of preparing the intermediate formulations, methods of preparing the finished pharmaceutical compositions, and methods of treating constipation and associated malfunctions of the human or animal body, which involves administering a laxative composition of this invention.

PREFERRED EMBODIMENTS

The particles of this invention are suitably in the size range 1 to 2000 μ, preferably 5 to 500 μ, more preferably 10 to 100 μ. They are employed in the manufacture of pharmaceutical compositions. The principal presentation is an oral tablet/capsule solid dosage form. An oral liquid presentation is also provided. A sachet-filled granule for reconstitution in liquids is another possibility within this invention. The particles are typically uncompressed particles, and for example do not take the form of tablets.

The stool softener is suitably poloxamer, though other possibilities include docusate sodium. The preferred product employs poloxamer, for instance with a bisacodyl:poloxamer ratio by weight of say 1:50 to 1:200, preferably about 1:100, as in 2.5 mg bisacodyl with 250 mg poloxamer or 5 mg bisacodyl with 500 mg poloxamer. A product employing docusate may include 30 mg to 50 mg docusate, for example in a bisacodyl:docusate weight ratio of say 1:5 to 1:250, such as 1:6 to 1:200, as in 2.5 mg bisacodyl with 30 mg or 100 mg docusate, or 5 mg bisacodyl with 250 mg or 500 mg docusate.

In the following discussion, the stool softener is poloxamer, but the methods and products can be modified for other stool softeners.

The pharmaceutical compositions of this invention have the active compound bisacodyl coated with an enteric coat such as enteric polymer to restrict contact between the drug and stomach wall and between the drug and the low pH gastric fluid, thereby overcoming the irritant nature of bisacodyl within the gastric region.

Various types of commercial enteric coating polymers are candidates for coating materials to make the enteric coated bisacodyl particles or tablets, including aqueous dispersions or organic solutions of enteric polymers such as methacrylic acid co polymers (Eudragit L or S), cellulose acetate phthalate, cellulose acetate butyrate, hydroxypropyl methyl cellulose phthalate, polyvinyl acetate phthalate etc.

Many of the commercial enteric coating polymers have the potential to interact with the bisacodyl, especially in the presence of moisture, for example during coating or forming operations. For example, there may be free carboxylic acid groups. Accordingly, particularly where stability tests suggest the need, we prefer to include a barrier coating before the enteric coating. The barrier coating is typically one which rapidly dissolves or disperses.

As an alternative to a barrier coating, it is possible to partially neutralise the free carboxylic acid groups and thereby reduce the potential interaction with bisacodyl. In this respect, the pH is usually brought up to as near to neutral as possible. Only partial neutralisation of the acid groups is possible when using bases containing alkali, alkali earth or other metal ions as these are not removed to enable acid groups to reform upon drying. For example, for Eudragit L 30 D-55 when using sodium hydroxide, the pH is taken to about pH 5, and the result is that about 6% of the free carboxylic acid groups are neutralised. When using a non-metal alkali such as ammonium hydroxide, the neutralisation can be taken further, since the ammonia can evaporate upon drying of the polymer. In this way, the invention can provide a bisacodyl product with an enteric coating directly applied to the bisacodyl, which product is substantially free from bisacodyl degradation products.

Therefore, in one embodiment, the invention provides a tablet comprising a core containing bisacodyl and having an enteric coat, wherein the enteric coat of the enteric coated bisacodyl is of partially-neutralised enteric material.

In another embodiment, the invention provides a tablet comprising a core containing bisacodyl and having an enteric coat, further comprising a barrier between the core and the enteric coat.

Furthermore, poloxamer has the potential to plasticise many of the commercial enteric coating polymers. Accordingly, particularly where stability tests suggest the need, we prefer to include an overcoat on the enteric coating. The overcoating is typically one which rapidly dissolves or disperses.

It is preferred to provide a product, which may be bisacodyl particles or bisacodyl tablets, having the barrier or the neutralised enteric coat, and/or the overcoat. Where both a barrier coat and an overcoat are included, they may be of the same or a different composition. The selection of excipients is made with regard to their compatibility with bisacodyl and other ingredients, and their status as well-established, readily available and commonly used materials with acceptable regulatory status and safety profiles.

Solid Dosage Form

The solid dosage form of this invention suitably comprises the enteric coated bisacodyl particles and a stool softener, preferably in unit dosage form. Suitable stool softeners include poloxamers such as poloxamer 188, as well as docusate sodium. The unit dose is preferably available in more than one strength, and for instance there can be 2 to 3 mg bisacodyl in a low dose form, and 4 to 6 mg bisacodyl in a high dose form.

It is possible but not currently preferred to prepare bisacodyl/poloxamer capsules containing 2.5/250 mg and 5/500 mg to a common formulation, encapsulated at different fill weights, using the techniques of EP 642,786. Suitable capsule sizes comprise size 1 and extended size 0 or smaller for the standard and strong presentations, respectively.

Sachet Filling of Enteric Coated Unit

Aqueous suspension development of a bisacodyl product is based on using the enteric coated particles. An aqueous dispersion of enteric-coated bisacodyl particles suspended in acidic media (e.g. citrus-flavoured) to preserve the enteric coat can be reconstituted from a dry powder. Suitable formulations might include diluents, such as lactose, sucrose, mannitol, sorbitol or poloxamer; flavouring agents; pH adjusters such as citric acid; or suspending agents such as HPMC, CMC or xanthan gum. The enteric coated bisacodyl particles and poloxamer can be granulated with other excipients, to give a free flowing powder that can be filled into sachets.

The product can be a sprinkle-on product or as particle/granule for reconstitution in liquid.

Aqueous Dispersion of Enteric Coated Unit

There is currently no oral liquid formulation of bisacodyl on the market, most probably because of the challenges associated with enteric coating of particles. Formulation of a dispersion at an acidic pH to preserve the enteric coat is the preferred approach. This formulation approach is also likely require such excipients as suspending agent, flavour and preservative.

Other Excipients

Additional excipients may be included in any pharmaceutical composition of this invention, as required, for example processing aids such as anti-oxidant, binder, suspending agent, flavour.

Pack Options

The present invention provides packs containing pharmaceutical compositions of this invention. Options include blister packs for capsules or tablets, sachets for granules for sprinkle-on or constitution in liquids and glass bottles for aqueous dispersion.

Shelf-Life

For solid dosage form products, a target of 18 months to 3 years at room temperature is desirable in a commercial product. For aqueous dispersion the corresponding target is 18 months to 2 years at room temperature.

In preferred embodiments of this invention, the amount of degradation products of bisacodyl after 3 months storage at 30° C. and 60% relative humidity is less than 0.5% by weight, usually 0.4% or less, e.g. 0.3% or less. The degradation products will generally be 4,4'-(2-pyridinylmethylene) bisphenol and 4,4'-(2-pyridinylmethylene) bisphenol.

The products of this invention may take many forms, and various manufacturing routes are available, as follows.

Enteric coated bisacodyl mini-tablets filled into a capsule followed by addition of molten poloxamer or vice versa.

Mini-tablets 1 to 5 mm in diameter can be manufactured by granulation or direct compression using excipients and processing techniques that are well known. Various conventional additives may be employed, for example: diluents such as lactose, microcrystalline cellulose, calcium phosphate; binders such as povidone, hypromellose, hydroxypropyl cellulose; disintegrants such as croscarmellose sodium, crospovidone, modified starch, starch; lubricants and glidants such as magnesium stearate, hydrogenated vegetable oil, sodium stearyl fumarate, colloidal anhydrous silica, talc. The powder blend or granulate can be compressed into tablets using conventional tabletting machines. The compressed tablets can then be enteric coated from either aqueous dispersions or organic solutions of enteric polymers, using traditional materials such as methacrylic acid co polymers (Eudragit L or S), cellulose acetate phthalate, cellulose acetate butyrate, hydroxypropyl methyl cellulose phthalate, polyvinyl acetate phthalate etc. Using a capsule machine equipped for handling both tablets and hot melt encapsulation, utilising two or more filling stations, an enteric coated tablet is filled into each capsule at the first station. The molten poloxamer is then filled into the capsules on top of the enteric coated tablet at the second filling station, and the capsule closed. Alternatively the poloxamer melt may be filled at the first filling station and the tablet added at the second station on the machine.

Enteric coated bisacodyl particles filled into capsules followed by addition of molten poloxamer or vice versa, and dispersion of enteric coated bisacodyl particles in molten poloxamer and filling the molten dispersion into capsules Enteric coated bisacodyl particles can be prepared by several technologies:

Spray Drying

The bisacodyl can be dissolved or dispersed in a solution of enteric polymer such as aqueous dispersions or organic solutions of enteric polymers, using traditional materials such as methacrylic acid co polymers (Eudragit L or S), cellulose acetate phthalate, cellulose acetate butyrate, hydroxypropyl methyl cellulose phthalate, polyvinyl acetate phthalate etc. Suitable organic solvents include for example methanol, ethanol, isopropanol, acetone, ethyl acetate, dichloromethane. Spray drying with organic solvents can avoid the need to protect the bisacodyl with a barrier coat. Optionally plasticizers such as triethyl citrate, triethyl acetate, polyethylene glycol, dibutyl sebaccate may be added. Optionally antitack/antiadherents such as talc, glycerol monostearate, colloidal anhydrous silica may be added. Suitable spray dryers would include those manufactured by DryTec or Niro. The solution or suspension may be atomised by an appropriate atomiser for example hydraulic, pneumatic, spinning disk or ultrasonic.

If the bisacodyl is suspended in a solution of the polymer and then spray dried the resulting particle will comprise a bisacodyl core with a coating of enteric polymer. Alternatively if the bisacodyl is dissolved in the polymer solution then the resulting particles will be a matrix of bisacodyl/enteric polymer. Alternatively by appropriate selection of a mixed solvent system, the drug may be dissolved initially but during the spray drying process precipitate before the enteric polymer to give a very fine dispersion of drug in the enteric polymer.

The drug may be present in either crystalline or amorphous form.

Melt Extrusion

The bisacodyl may be mixed with enteric polymers, such as methacrylic acid co polymers (Eudragit L or S), cellulose acetate phthalate, cellulose acetate butyrate, hydroxypropyl methyl cellulose phthalate, polyvinyl acetate phthalate etc. The drug/polymer mix is then extruded into fine strands using for example a twin screw extruder such as those made by Leisteritz or Brabender. The resulting extrudate can either be cut into short lengths or milled into fine particles. The bisacodyl is thus intimately mixed and incorporated into the enteric polymer under the force of heat and pressure during the melt extrusion process. Optionally plasticisers, lubricants and diluents may be added to facilitate processing.

The particles may optionally be overcoated with further enteric polymer, with or without addition of other ingredients such as plasticisers, anti-tack agents, anti-adherent agents, etc.

The drug may be present in either crystalline or amorphous form.

Co-acervation

The bisacodyl can be dissolved or dispersed in a suitable solvent. The enteric polymer is dissolved in a suitable organic solvent or may be used as an aqueous dispersion, using traditional materials such as methacrylic acid co polymers (Eudragit L or S), cellulose acetate phthalate, cellulose acetate butyrate, hydroxypropyl methyl cellulose phthalate, polyvinyl acetate phthalate etc. Suitable organic solvents include for example methanol, ethanol, isopropanol, acetone, ethyl acetate, dichloromethane. Optionally plasticizers such as triethyl citrate, triethyl acetate, polyethylene glycol, dibutyl sebaccate may be added. Optionally antitack/antiadherents such as talc, glycerol monostearate, colloidal anhydrous silica may be added. The solution of drug and polymer are emulsified such that the drug substance is coated with/precipitates in the solution/dispersion of enteric polymer. Whilst mixing the solvents are removed by evaporation or extraction into another solvent in which both the drug substance and polymer are essentially insoluble. The coated drug particles are then collected by sieving/screening and dried to remove residual solvents If the bisacodyl is suspended in one phase and emulsified with a solution of the polymer in another phase then the resulting particle will comprise a bisacodyl core with a coating of enteric polymer. Alternatively if the bisacodyl is dissolved and mixed with the polymer solution then the resulting particles will be a matrix of bisacodyl/enteric polymer. Alternatively by appropriate selection of a mixed solvent system, the drug may be dissolved initially but during the mixing process precipitate before the enteric polymer to give a very fine dispersion of drug in the enteric polymer.

The different coats can be applied either step-wise by carrying out each coating procedure, recovering the coated particles, and then appying another coating procedure, in appropriate solvent/suspension systems or by using multiphase systems, for instance by making an emulsion of the drug in oil with water outside containing a water or acid soluble coating agent, eg HPMC, which system is then dispersed in another oil phase containing an organic solvent and enteric polymer, and then removing the solvents in known manner by evaporation/extraction as appropriate.

The drug may be present in either crystalline or amorphous form.

Fluid Bed Coating

The bisacodyl particles, suitably of size 500 μm or less, may be coated with enteric polymer such as aqueous dispersions or organic solutions of enteric polymers, using traditional materials such as methacrylic acid co polymers (Eudragit L or S), cellulose acetate phthalate, cellulose acetate butyrate, hydroxypropyl methyl cellulose phthalate, polyvinyl acetate phthalate etc. Suitable organic solvents include for example methanol, ethanol, isopropanol, acetone, ethyl acetate, dichloromethane. Optionally plasticizers such as triethyl citrate, triethyl acetate, polyethylene glycol, dibutyl sebaccate may be added. Optionally antitack/antiadherents such as talc, glycerol monostearate, colloidal anhydrous silica may be added. The coating may be applied using a fluidized bed coater such as those manufactured by Glatt or Aeromatic, using for example Wurster, high speed Wurster or tangential spray systems. Fluidized bed coating may typically be utilised for drug particles of 80 μm and above but with careful control may also be applicable for smaller particles.

Granulation Method

As an alternative to powder coating, coating of small particle size granules may be acceptable. Active granules may be produced either by wet granulation or roller compaction and milling. In the case of wet granulation, the enteric polymer dispersion/solution can be used as the binding agent or alternatively this can be replaced with a conventional binder. Dense granules/spheroids may also be formed by extrusion technology with or without spheronisation. Using either of these techniques, the produced granules are characterised by their high density, small surface area, uniform shape and narrow size distributions. Granules/spheroids can then be coated with the enteric polymer dispersion/solution in a fluid bed coating apparatus. Efficient spray coating can be facilitated by the granule/spheroid characteristics. A further extension of this approach, where variability in enteric coating of granules or spheroids is a problem, is the compression of granules into mini-tablets to increase the reproducibility prior to coating.

Alternative to Molten Poloxamer

As an alternative to using molten poloxamer in capsule fillings, poloxamer in the form of free flowing granules may be used together with enteric coated bisacodyl particles or mini tablets to powder fill capsules or sachets. The poloxamer particles are suitably of size 500 μm or less.

With this alternative, one of the problems found when bringing poloxamer particles into contact with the enteric coat of the tablet is that the poloxamer particles stick to the enteric material and the poloxamer has a plasticiser effect upon the coat. When the poloxamer is removed/dissolved there consequently is a weakened area in the enteric coat or the coating may even be partially lost. This weakening leads to release of the active ingredient even at acid pH. For this reason, we prefer that a protective coating is applied over the enteric coating. This coat protects the enteric material from the poloxamer, and usually will be instantly dispersible upon contact with water. Any water-soluble cellulose or other coating material could be used. Other coating materials are, for example, water or acid soluble acrylic polymers, e.g. Eudragit E, polyvinyl alcohol, and polyvinyl pyrrolidone. Suitable water soluble celluloses in addition to HPMC are hydroxypropyl cellulose, methyl cellulose and sodium carboxymethyl cellulose. For the present, we prefer hydroxypopylmethyl cellulose with a small amount of triethylcitrate as plasticiser.

As explained, the enteric material has the potential to catalyse degradation of bisacodyl at raised temperatures and in the presence of moisture. In order to avoid this problem, a partially neutralised form of enteric material can be used. Thus, the enteric material typically has free carboxyl groups, such as occur with the Eudragits. The Eudragit material obtainable from the manufacturers has pH 2.5 to 2.7. In this respect, the pH is usually brought up to as near to neutral as possible. Only partial neutralisation of the acid groups is possible when using bases containing alkali, alkali earth or other metal ions as these are not removed to enable acid groups to reform upon drying. For example, when using sodium hydroxide, the pH is taken to about pH 5, and the result is that about 6% of the free carboxylic acid groups are neutralised. When using a volatile alkali such as ammonium hydroxide, the neutralisation can be taken further, since the ammonia can evaporate upon drying of the polymer.

Thus, in one aspect, we provide enteric coated bisacodyl particles or tablets with a partially neutralised enteric coat and a protective top coat.

Another formulation uses a first water-soluble protective coat applied directly to the tablet core. An enteric coating, which need not be neutralised, is applied and this is covered with a further, protective top coat. Thus, in a second aspect, we provide enteric coated bisacodyl particles or tablets with a first water-soluble protective coat, an enteric coat and a protective top coat.

The current formulations use a coating weight of up to 6%, say about 2% for the protective coatings (each, in the triple coat) and up to 20%, for example 5 to 20%, say about 10% for the enteric coat. The coating weights are expressed as a percentage by weight of the tablet or partially coated tablet being coated. In general, a higher coating weight percentage is applied for smaller tablets, and correspondingly a lower coating weight percentage for bigger tablets.

We have found it particularly advantageous to include a disintegrant such as Ac-di-Sol in the bisacodyl cores of the particles of this invention. Ac-di-Sol is croscarmellose sodium, a super-disintegrant, for ensuring the rapid and reproducible disintegration of the core after the enteric coat has dissolved. The aim is to achieve a rapid release, typically at least 80% dissolution of the bisacodyl in 45 minutes at pH 6.8.

EXAMPLES OF THE INVENTION

Figure 1:
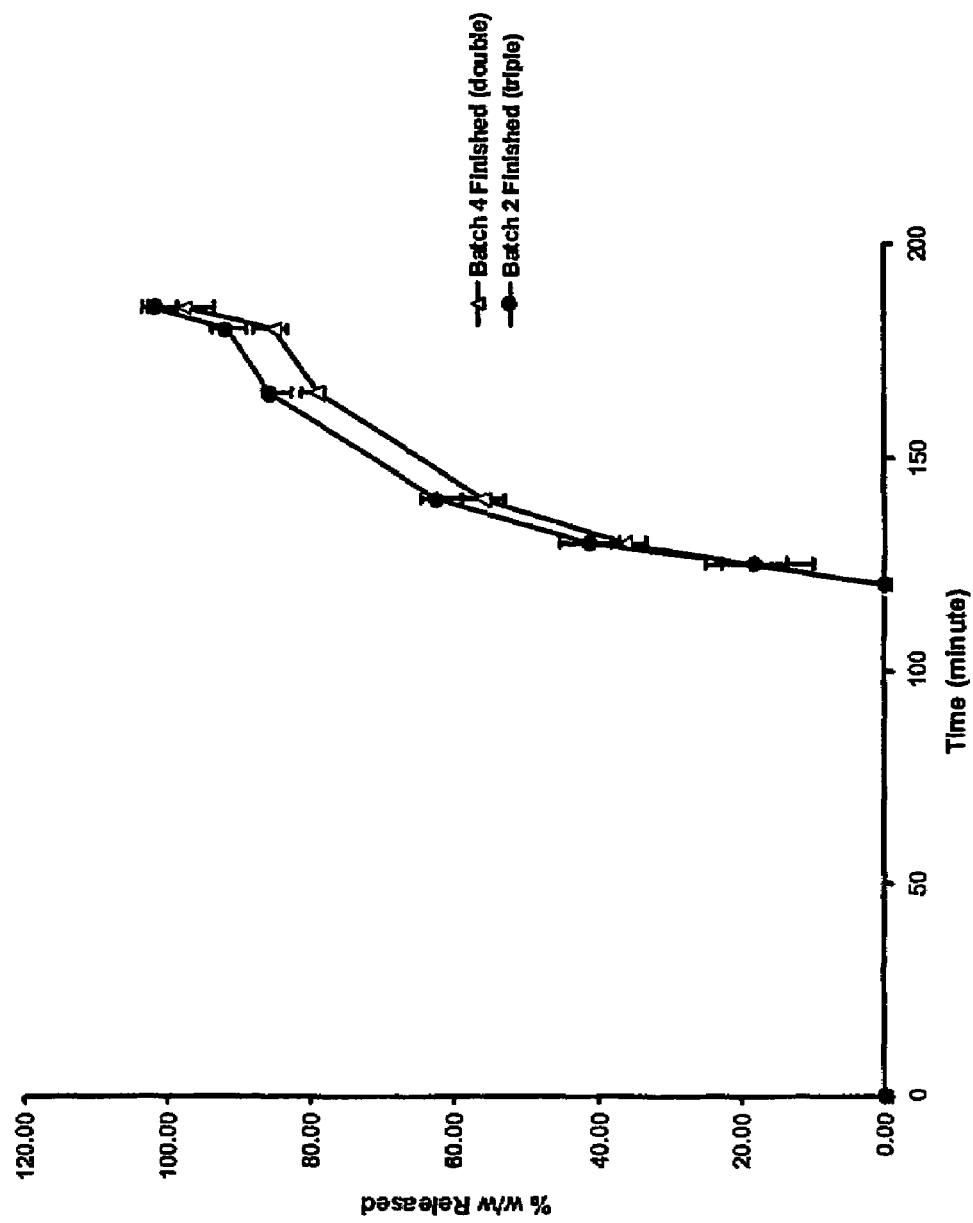
FIG. 1 shows the release rate and prfile of bisacodyl 5.0 mg enteric coated tablets made on a pilot scale.

The present invention is illustrated by the following examples.

Example 1

Bisacodyl is screened to produce particles less that 45 microns which are then mixed with Eudragit L100-55 polymer in the ratio 1 to 10 drug to polymer (ie 10% drug loading) and dispersed in ammonium hydroxide solution (0.05M) in which the polymer, but not the drug, is soluble. On spray drying the polymer forms a coat on the bisacodyl particle.

Example 2

Triple coat 2.5 mg bisacodyl, 250 mg poloxamer capsules core formulation, quantities mg/tablet

| | |
|---|---|
| Bisacodyl | 2.50 |
| Microcrystalline cellulose, Avicel* PH 101 | 15.85 |
| Lactose anhydrous | 15.85 |
| Croscarmellose sodium, Ac-Di-Sol* | 0.40 |
| Magnesium stearate | 0.40 |
| | 35.00 |

*Avicel and Ac-Di-Sol are registered trade marks of FMC Corporation.

enteric coat formulation, quantities mg/tablet

| | | |
|---|---|---|
| Eudragit L 30 D-55** | 2.79 | |
| Triethyl citrate | 0.560 | |
| Aerosil 200 | 0.140 | |
| Purified water | QS | |

**as 30% w/w suspension protective coat formulation, quantities mg/tablet

| | | |
|---|---|---|
| HPMC E5 | 0.630 | |
| Triethyl citrate | 0.070 | |
| Purified water | QS | |

Filled capsules are made according to the following procedure:

1. Blend all tablet core components except the magnesium stearate in a suitable blender (e.g. Y-cone) for 10 minutes. Add magnesium stearate and blend for a further 5 minutes.
2. Compress the blend using 4.0 mm round normal concave tooling at a tablet weight of 35 mg, hardness not less than 2.0 kp on a suitable rotary compression machine (e.g. Fette 1200 )
3. Prepare the HPMC protective coating solution.
4. Coat the tablets with HPMC coat using a suitable drum coater (e.g. Manesty Accela Cota) until an approximately 2% increase in tablet weight has been achieved (approx. 60-100 minutes). Allow to dry.
5. Prepare the Eudragit enteric coating dispersion.
6. Coat the tablets with enteric coat until an approximately 10% increase in coated tablet weight has been achieved (approx. 150-200 minutes). Allow to dry.
7. Coat the tablets with a coat of HPMC solution until an additional approximately 2% increase in tablet weight has been achieved (approx. 60-100 minutes). Allow to dry.
8. Lubricate Poloxamer 188 with 1% magnesium stearate by blending for 10 minutes in a suitable blender (e.g. Y-cone).
9. Fill size 1 capsules with one Bisacodyl 2.5 mg coated tablet followed by 253 mg lubricated Poloxamer 188 using an appropriate capsule filler fitted with a dual filling attachment (e.g. Bosch 1500 provided with dual tablets and powder filling mechanism).

A batch of the capsules was given the designation Batch 1.

Example 3

Triple coat 5 mg bisacodyl, 500 mg poloxamer capsules
core formulation, quantities mg/tablet

| | | |
|---|---|---|
| Bisacodyl | 5.00 | |
| Avicel PH 101 | 14.6 | |
| Lactose anhydrous | 14.6 | |
| Ac-Di-Sol | 0.40 | |
| Magnesium stearate | 0.40 | |
| | 35.00 | |

The procedure of Example 2 is repeated, but in using size extended 0 (OE) capsules and filling with 505 mg of lubricated Poloxamer 188.

A batch of the capsules was given the designation Batch 2.

Example 4

Double coat 2.5 mg bisacodyl, 250 mg poloxamer capsules
The procedure of Example 2 is repeated, but excluding step 4 and, in step 5, a 1 molar sodium hydroxide solution is used for partial neutralisation of the Eudragit L 30 D-55 dispersion to pH 5.0 before mixing with other ingredients.

A batch of the capsules was given the designation Batch 3.

Example 5

Double coat 5 mg bisacodyl, 500 mg poloxamer capsules
The procedure of Example 3 is repeated with the modifications of Example 3.

A batch of the capsules was given the designation Batch 4.

Example 6

Figure 2:
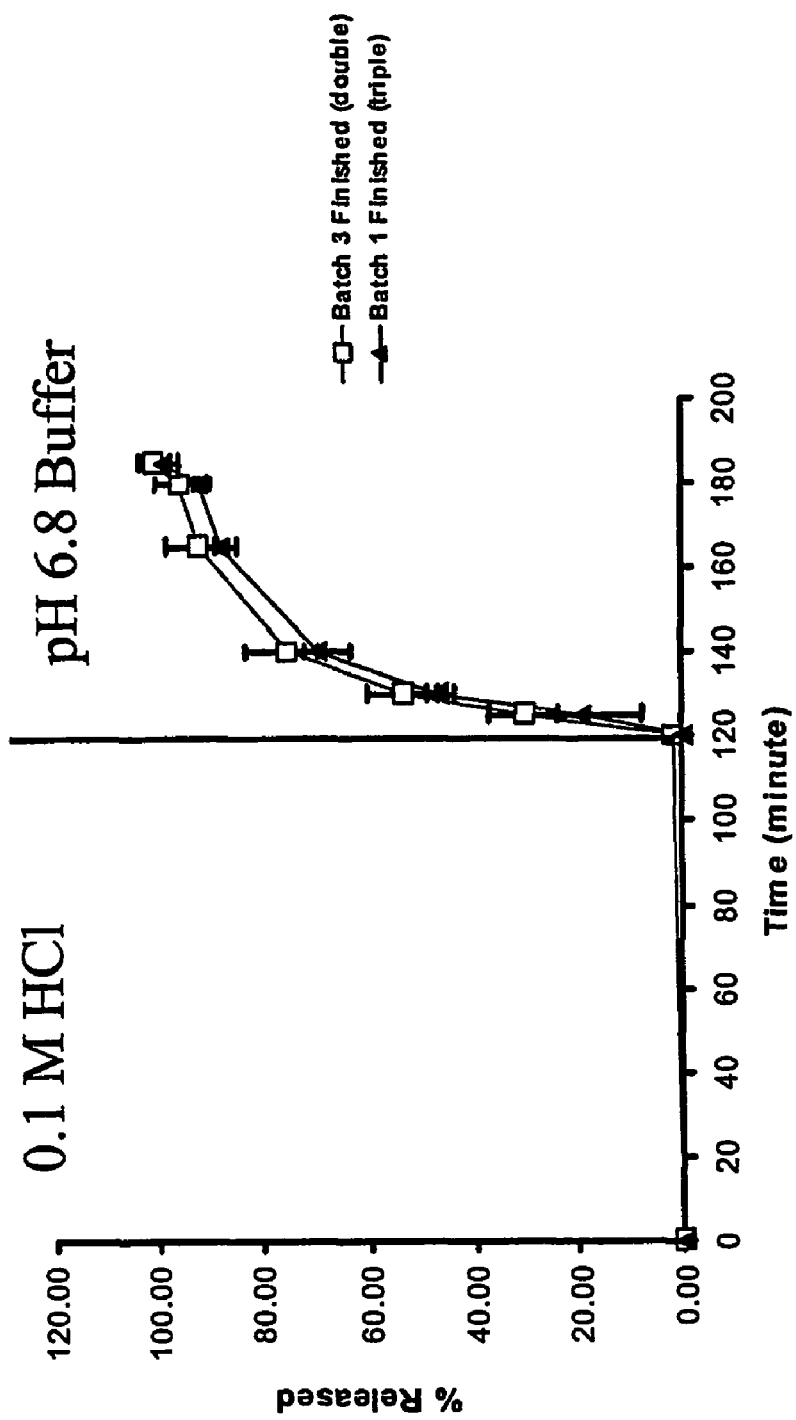
FIG. 2 shows the release rate and prfile of bisacodyl 2.5 mg enteric coated tablets made on a pilot scale.

Release Rates and Profiles
FIGS. 1 and 2 show release rate data for the respective batches produced in Examples 2 to 5, determined according to USP XXV oage 2017 "Delayed Release Enteric Coated Particles—General Drug Release Standard", but with 0.55% w/v sodium lauryl sulphate (SLS) in phosphate buffer at pH 6.8.

Example 7

A sample of the capsules designated Batch 1 of Example 2 were assayed to give the results shown for the Initial Analysis in the following tables. Batch 1 capsules were packaged in PVdC coated PVC blisters with aluminium foil backing and subjected to stability studies, giving the results shown in the following tables after 3 months at 30° C. and 60% relative humidity:

(a) Analytical Data

| Product: Bisacodyl/Poloxamer Capsules 2.5 mg/250 mg Batch: 1 Container: PVdC coated PVC blister with aluminium backing foil | | |
|---|---|---|
| | INITIAL ANALYSIS | 3 MONTHS |
| BISACODYL (mg/tab) | 2.45 | 2.47 |
| POLOXAMER (mg/tab) | 253.4 | 249.4 |
| TOTAL DEGRADATION PRODUCTS (% w/w) | 0.26 | 0.30 |
| TOTAL SYNTHETIC IMPURITIES (% w/w) | 0.10 | 0.10 |
| TOTAL RELATED SUBSTANCES (% w/w) | 0.35 | 0.40 |
| MOISTURE - BISACODYL (% w/w) | 2.5 | 3.0 |
| MOISTURE - POLOXAMER (% w/w) | 0.5 | 0.6 |
| TABLET HARDNESS (kp) | 7 | 7 |

| Product: Bisacodyl/Poloxamer Capsules 2.5 mg/250 mg Batch: 1 Container: PVdC coated PVC blister with aluminium backing foil ||| 
|---|---|---|
| DISSOLUTION OF BISACODYL (MEAN) | INITIAL ANALYSIS | 3 MONTHS |
| 120 mins | 0 | 0 |
| 125 mins | 19 | 23 |
| 130 mins | 47 | 50 |
| 140 mins | 69 | 73 |
| 165 mins | 88 | 91 |
| 180 mins | 92 | 95 |
| >180 mins | 99 | 99 |

| Product: Bisacodyl/Poloxamer Capsules 2.5 mg/250 mg Batch: 1 Container: PVdC coated PVC blister with aluminium backing foil ||||
|---|---|---|---|
| DISSOLUTION OF POLOXAMER (MEAN) | INITIAL ANALYSIS | 2 MONTHS | 3 MONTHS |
| 10 mins | 22 | — | 19 |
| 20 mins | 68 | — | 67 |
| 30 mins | 94 | — | 95 |
| 45 mins | 101 | — | 101 |
| 60 mins | 101 | — | 102 |

Comments

No change in bisacodyl content form initial (2.47 mg/tablet). No significant increase in total related substances (0.40% w/w). Bisacodyl dissolution showed no change from initial (0% released in acid, 91% released after 45 minutes in pH 6.8 buffer). 2% decrease in the poloxamer content from initial (249.4 mg/capsule). Poloxamer dissolution analysis showed no change from initial (101% released after 45 minutes). A slight increase in moisture content was observed from both bisacodyl and poloxamer. No significant change for the remaining tests compared with initial.

Example 8

In the same way the stability of Batch 2 from Example 3 was investigated and gave the results in the following tables:

a) Analytical Data

| Product: Bisacodyl/Poloxamer Capsules 5.0 mg/500 mg Batch: 2 Container: PVdC coated PVC blister with aluminium backing foil |||
|---|---|---|
|  | INITIAL ANALYSIS | 3 MONTHS |
| BISACODYL (mg/tab) | 5.01 | 4.86 |
| POLOXAMER (mg/cap) | 502.7 | 500.4 |
| TOTAL DEGRADATION PRODUCTS (% w/w) | 0.25 | 0.26 |
| TOTAL SYNTHETIC IMPURITIES (% w/w) | 0.10 | 0.10 |
| TOTAL RELATED SUBSTANCES (% w/w) | 0.34 | 0.35 |
| MOISTURE - BISACODYL (% w/w) | 2.5 | 2.6 |
| MOISTURE - POLOXAMER (% w/w) | 0.7 | 0.6 |
| TABLET HARDNESS (kp) | 8 | 8 | b) Bisacodyl Dissolution

| Product: Bisacodyl/Poloxamer Capsules 5.0 mg/500 mg Batch: 2 Container: PVdC coated PVC blister with aluminium backing foil |||
|---|---|---|
| DISSOLUTION OF BISACODYL (MEAN) | INITIAL ANALYSIS | 3 MONTHS |
| 120 mins | 0 | 0 |
| 125 mins | 18 | 17 |
| 130 mins | 41 | 41 |
| 140 mins | 62 | 62 |
| 165 mins | 86 | 85 |
| 180 mins | 92 | 91 |
| >180 mins | 102 | 101 | c) Poloxamer Dissolution

| Product: Bisacodyl/Poloxamer Capsules 5.0 mg/500 mg Batch: 2 Container: PVdC coated PVC blister with aluminium backing foil |||
|---|---|---|
| DISSOLUTION OF POLOXAMER (RANGE) | INITIAL ANALYSIS | 3 MONTHS |
| 10 mins | 16-24 | 12-23 |
| 20 mins | 53-76 | 52-66 |
| 30 mins |  | 78-94 |
| 45 mins | 101-103 | 99-103 |
| 60 mins | 101-103 | 100-104 |

Comments

3% decreased in bisacodyl content from initial (4.86 mg/tablet). No significant increase in total related substances (0.35% w/w), 4,4-(2-pyridinyl methylene bisphenol was detected. Bisacodyl dissolution showed no change from initial (0% released in acid, 85% released after 45 minutes in pH 6.8 buffer). No change in the poloxamer content from initial (500.4 mg/capsule). Poloxamer dissolution analysis showed no change from initial (102% released after 45 minutes). No significant change for the remaining tests compared with initial.

The invention claimed is:

1. A pharmaceutical composition comprising poloxamer and bisacodyl, wherein the bisacodyl in a single dosage form is coated with an enteric coat, and a protective overcoat is coated on the enteric coat to stabilize the enteric coat from plasticization by the poloxamer, wherein said enteric coat and said protective overcoat separate poloxamer from the bisacodyl.

2. A pharmaceutical composition according to claim 1, wherein the bisacodyl coated with the enteric coat is in the form of a tablet.

3. A pharmaceutical composition according to claim 2, wherein the tablet comprises compressed enteric coated bisacodyl particles or a compressed core containing bisacodyl and having an enteric coat.

4. A pharmaceutical composition according to claim 3, wherein the tablet is a mini-tablets of 1 to 5 mm in diameter.

5. A pharmaceutical composition according to claim 1, in the form of a filled capsule.

6. A pharmaceutical composition according to claim 5, wherein the capsule is filled with poloxamer in molten or particulate form, and with the bisacodyl coated with an enteric coat.

7. A pharmaceutical composition according to claim 1, wherein the enteric coat is of partially neutralized enteric material.

8. A pharmaceutical composition according to claim 1, with a barrier coat between the bisacodyl and the enteric coat.

9. A pharmaceutical composition according to claim 1, having a weight ratio of bisacodyl:poloxamer from 1:50 to 1:200.

10. A pharmaceutical composition according to claim 1, in the form of a sachet with a fill of particles of the bisacodyl coated with an enteric coat and particles of poloxamer, for reconstitution in water.

11. A pharmaceutical composition according to claim 1, in the form of a liquid dispersion.

12. A pharmaceutical composition according to claim 8, wherein the barrier coat and the protective overcoat are of the same or different composition.

13. A pharmaceutical composition according to claim 1, wherein the bisacodyl is in the form of particles coated with an enteric coat.

14. The composition of claim 1, wherein the poloxamer is a stool softener.

* * * * *